US008795707B2

(12) United States Patent
Wolinsky et al.

(10) Patent No.: US 8,795,707 B2
(45) Date of Patent: Aug. 5, 2014

(54) COMPLIANT COMPOSITES FOR APPLICATION OF DRUG-ELUTING COATINGS TO TISSUE SURFACES

(75) Inventors: Jesse Wolinsky, Brookline, MA (US); Mark W. Grinstaff, Brookline, MA (US); Yolonda L. Colson, Dover, MA (US)

(73) Assignees: Trustees of Boston University, Boston, MA (US); The Brigham and Women's Hospital, Inc., Boston, MA (US)

( * ) Notice: Subject to any disclaimer, the term of this patent is extended or adjusted under 35 U.S.C. 154(b) by 594 days.

(21) Appl. No.: 12/991,944

(22) PCT Filed: May 7, 2009

(86) PCT No.: PCT/US2009/043089
§ 371 (c)(1),
(2), (4) Date: Mar. 9, 2011

(87) PCT Pub. No.: WO2009/140131
PCT Pub. Date: Nov. 19, 2009

(65) Prior Publication Data
US 2011/0172785 A1 Jul. 14, 2011

Related U.S. Application Data

(60) Provisional application No. 61/052,964, filed on May 13, 2008.

(51) Int. Cl.
*A61F 2/00* (2006.01)
*A61L 15/16* (2006.01)
(52) U.S. Cl.
USPC .......................................... 424/423; 424/447
(58) Field of Classification Search
CPC .......... A61L 31/10; A61L 29/04; A61L 29/06
USPC ....................................................... 424/423
See application file for complete search history.

(56) References Cited

U.S. PATENT DOCUMENTS

| | | | |
|---|---|---|---|
| 3,305,605 A | 2/1967 | Hostettler et al. |
| 3,324,070 A | 6/1967 | Cox et al. |
| 3,379,693 A | 4/1968 | Cox et al. |
| 4,900,785 A | 2/1990 | Leitz et al. |
| 4,908,416 A | 3/1990 | Eichenauer et al. |
| 4,912,168 A | 3/1990 | Eichenauer et al. |
| 4,965,300 A | 10/1990 | Eichenauer et al. |
| 5,634,931 A | 6/1997 | Kugel |
| 5,824,082 A | 10/1998 | Brown |
| 6,093,792 A | 7/2000 | Gross et al. |
| 6,114,458 A | 9/2000 | Hawker et al. |
| 6,280,453 B1 | 8/2001 | Kugel |
| 6,734,257 B2 | 5/2004 | Windisch et al. |
| 7,671,095 B2 | 3/2010 | Colson et al. |
| 2002/0032414 A1 | 3/2002 | Ragheb et al. |
| 2004/0063200 A1 | 4/2004 | Chaikof et al. |
| 2004/0167276 A1 | 8/2004 | Windisch et al. |
| 2005/0019404 A1 | 1/2005 | Sung et al. |
| 2007/0077272 A1 | 4/2007 | Li et al. |
| 2007/0141112 A1 | 6/2007 | Falotico et al. |
| 2008/0075718 A1 | 3/2008 | Colson et al. |

FOREIGN PATENT DOCUMENTS

| | | |
|---|---|---|
| FR | 1426964 | 3/1965 |
| FR | 1434145 | 3/1965 |
| WO | WO 2004028269 | 4/2004 |
| WO | WO 2006/036130 | 4/2006 |
| WO | WO 2007/140483 | * 12/2007 |
| WO | WO 2009140131 | 11/2009 |

OTHER PUBLICATIONS

He et al. (Macromolecules, 38, 8227-8234, 2005) Synthesis and Charcterization of functionalization . . . .*
He et al. "Synthesis and Characterization of Functionalizable and Photogpatternable Poly(-caprolactone-copRS-beta-malic acid)," *Macromolecules* 38, 8227-8234 (2005).
Wolinsky et al., "Prevention of in vivo lung tumor growth by prolonged local delivery of hydroxycamptothecin using poly(ester-carbonate)-collagen composites", *Journal of Controlled Release* 144 (2010) 280-287.
Adusumilli et al., "Intraoperative localization of lymph node metastases with a replication-competent herpes simplex virus", J. Thorac Cardiovasc. Surg., 132:1179-88 (2006).
Agrawal et al., J. Biomaterials, 13:176-182 (1992).
Athanasiou et al., Arthroscopy, 14:726-737 (1998).
Attawia et al., "Cytotoxicity testing of poly(anhydride-co-imides) for orthopedic applications", J. Biomed. Mater. Res., 29:1233-140 (1995).
Azouz, et al., "Prevention of local tumor growth with paclitaxel-loaded microspheres", J. Thorac. Cardiovasc. Surg., 2008;135:1014-1021.
Black et al., Polymerisation of Unsaturadted Derivative of 1,2:5, 6-DI-O-isopropylidene-D-glucofuranose, J. of the Chem. Soc., 4433-4439 (1963).
Chiu et al., J. "Synthesis Functional Poly(carbonate-b-ester) Copolymers and Micellar Characterizations", Applied Polymer Science, 106(1):283-292 (2007).
Compan et al., "Response of Acrylate Polymers Containing Substituted 1, 3-Dioxacycloheane Groups in the Ester Residue to Mechanical and Electric Perturbation Fields", Polymer, 42(9):4339-4346 (2001).
Diaz-Calleja et al, "Comparative Study of Mechanical and Dielectric Properties of Glassy Acrylic Polymers Containing 1, 3-Dioxane Rings in Their Structures", Macromolecular Symposia, 147:191-199 (1999).

(Continued)

*Primary Examiner* — David J Blanchard
*Assistant Examiner* — Tigabu Kassa
(74) *Attorney, Agent, or Firm* — Fish & Richardson P.C.

(57) ABSTRACT

A compliant composite for delivering a bioactive agent including a scaffolding material and a polymer coating that together can be attached to compliant tissue surfaces is disclosed, along with methods for constructing and applying these composites. In some embodiments, the composite further comprises a barrier layer for localized delivery of the bioactive agent.

13 Claims, 5 Drawing Sheets

(56) References Cited

OTHER PUBLICATIONS

Diaz-Calleja et al., "Comparative Study of the Relaxation Behavior at Very Low Frequencies of Acrylate Polymers with Pendant 1,3-Dioxane rings in their Structure", J. Applied Physics 84(8):4436-4442 (1998).

Diaz-Calleja et al., "Dielectric Relaxations in Polymers Containing Dioxacyclohexane Rings by Thermostimulated Depolarization Currents", Macromolecular Symposia, 191: 177-190 (2003).

Edlund et al., "Degradable polymer microspheres for controlled drug delivery", Adv. Polymer Sci., 157:67-112 (2001).

Garcia et al., "Relaxation Behavior of Acrylate and Methacrylate Polymers Containing Dioxacyclopentane Rings in the Side Chains", J. Polymer Science, Part B: Polymer Physics 39(3):286-299 (2001).

Gautam, et al., "Inhibition of experimental lung metastasis by aerosol delivery of PEI-p53 complexes", Mol. Ther. (2000) 2(4):318-23 (abstract only 1 page).

Gillies et al., "Stimuli-Responsive Supramolecular Assemblies of Linear-Dendritic Copolymers", J. Am. Chem. Soc., 126:11936-43 (2004).

Heller et al., "Poly(ortho esters): synthesis, characterization, properties and uses", Adv. Drug Deliv. Rev., 54:1015:1039 (2002).

IUPAC-IUB Commission on Biochemical Nomenclature, Biochem., 11:942-944 (1972).

Jemal et al., "Cancer Statistics", CA Cancer J. Clin., 56:106-130 (2006).

Laguna et al., "Experimental and Theoretical Studies on the Permeation of Argon Through Matrixes of Acrylic Polymers Containing 1, 3-Dioxane Groups in Their Structure", J. Chemical Physics, 110(6):3200-3206 (1999).

Landfester et al., "Formulation and stability mechanisms of polymerizable miniemulsions", Macromolecules, 32:5222-8 (1999).

Legrand, et al., "Side-Chain Liquid Crystalline Polyacrylates Containing Heterocyclic Phenyl Groups on the Mesomorphouse Properties", Makromol. Chem., Dec. 1990, vol. 191, No. 12 pp. 2971-2978.

Leitz et al., Mixtures of Aromatic Polycarbonates and/or Aromatic Polyesters With Special Copolymers, *Off. Gaz.* ISSN: 0360-5132 (1990) pp. 1064-1065.

Mantell et al., "Synthesis and Cross-linking of a New Series of Acrylate Polymers Containing m-dioxane Rings", J. Applied Polymer Science 9(11):3625-33 (1965).

Matsuda et al., "Short Communication; New Infusion Device for Trans-tissue, Sustained Local Delivery of Anticancer Agent to Surgically Resected Tissue: Potential Use for Suppression of Local Recurrence of Pancreatic Cancer", Published Online Dec. 30, 2004, Wiley InterScience (www.interscience.wiley.com). DOI:10.1002/jbm.b.30186, pp. 203-207.

Miller and Williams, Biomaterials, 8:129-137 (1987).

Mullen et al., "New Aliphatic Poly(ester-carbonates) Based on 5-Methyl-5-Allyloxycarbonyl-2,3- Dioxan-2-one", J. Polymer Science, Part A: Polymer Chemistry 41(13):1978-1991 (2003).

Qadri et al., "Can Surgery for Cancer Accelerate the Progression of Secondary Tumors Within Residual Minimal Disease at Both Local and Systemic Levels", Ann Thorac Surg, 80:1046-51 (2005).

Ruel-Gariépy et al., "A thermosensitive chitosan-based hydrogel for the local delivery of paclitaxel", European J. of Pharmaceutics and Biopharmaceutics 57 (2004) pp. 53-63.

Saiz et al., J. "Molecular Dynamics Simulations of the Time Dependent Dipolar Correlation Function for Esters Containing Substituted 1, 3-Dioxacyclohexane Rings in Their Structure", Physical Chemistry B, 101(50):10949-10953 (1997).

Sambrook et al., *Molecular Cloning: A Laboratory Manual* (2d ed., Cold Spring Harbor Laboratory Press, Cold Spring Harbor, N.Y. (1989) (not filed herewith—too voluminous—will be provided upon request).

Sperling, L. H. et al, "Nomenclature in Polymer Science and Engineering", Chem. Abstracts Serv., First Published: ACS Division of Polymeric Materials: Science and Engineering (PMSE), 68, 341 (1993) downloaded on Sep. 18, 2009 http://www.polyacs.org/nomcl/pmse.noml.html (3 pp.).

Storey et al., "Synthesis of Novel Hydrophilic Poly(ester-carbonates) Containing Pendent Carboxylic Acid Groups", J. Macromolecular Science, Pure and Applied Chemistry A38(9), 897-917 (2001).

Wang et al., "Preparation and characterization of poly(lactic-co-glycolic acid) microspheres for targeted delivery of a novel anticancer agent, taxol.", Chem. Pharm. Bull., (Tokyo) 44:1935 (1996).

Wang, et al., "Synthesis and Characterization of Amphiphilic Block Copolymer Containing PVP and Poly(5-benzyloxytrimethylene carbonate", vol. 17, No. 2, pp. 239-242 (2006).

Wolinsky, et al., "Inhibition of In Vivo Tumor Growth by Prolonged Local Delivery of a Chemotherapeutic using Poly(ester-carbonate)-collagen Composites", Journal of Controlled Release 144 (2010) 280-287.

Wolinsky, et al., "Poly(carbonate ester)s Based on Units of 6-Hydroxyhexanoic Acid and Glycerol", Macromolecules 40:7065-68 (2007).

Zheng et al., *Acetal Copolymers: Syntheses and Modification*, Dissertation Abstracts International, vol. 55, No. 11B, p. 4877 (1994).

International Preliminary Report on Patentability dated Nov. 17, 2010, PCT/US2009/043089 7 pages.

International Search Report and Written Opinion, mailing date Jan. 6, 2010, PCT/US2009/043089 13 pages.

Extended European Search Report in European Application No. 09747216.1, dated Apr. 16, 2013, 9 pages.

Walpole et al., "QS434. Localized Drug Delivery Through the use of Chemotherapy-Loaded Polymer Films," *J Surgical Res.*, 2008, 144(2):440.

\* cited by examiner ns is a §371 National Stage Application of International Application No. PCT/US2009/043089, filed May 7, 2009, which claims the benefit of priority of U.S. Provisional Application No. 61/052,964, filed May 13, 2010, each of which is incorporated herein by reference in its entirety.

COMPLIANT COMPOSITES FOR APPLICATION OF DRUG-ELUTING COATINGS TO TISSUE SURFACES

This application is a §371 National Stage Application of International Application No. PCT/US2009/043089, filed May 7, 2009, which claims the benefit of priority of U.S. Provisional Application No. 61/052,964, filed May 13, 2010, each of which is incorporated herein by reference in its entirety.

TECHNICAL FIELD

This invention relates to delivery systems for bioactive agents, and more particularly to composite systems for drug delivery.

BACKGROUND

The preferred first line of care for treating localized solid tumors is surgical removal, where the benefit of removing all of the cancer and surrounding tissue is balanced against the resultant morbidity to the patient. Given that microscopic disease can be present despite a complete surgical resection, surgery is often "augmented" with radiation and/or chemotherapy in an attempt to prevent recurrent cancer. Despite this aggressive approach, tumor recurrence is a major concern following primary treatment for many cancers including head, breast, lung, colon, rectal, and pancreatic malignancies. Recurrence can occur at a distant site due to cell migration or metastasis, pre-existing micrometastases missed at the time of the initial diagnosis, or microscopic disease that remains near the resection margins of the primary tumor.

In patients unable to tolerate surgery or if there is a particularly high risk of recurrence due to aggressive pathology or positive margins, treatment commonly includes external radiation therapy or chemotherapy. Several large clinical trials have indicated a potential survival benefit with adjuvant chemotherapy compared to observation alone following surgery for early stage lung cancer, however, such treatment has not become the standard of care as the overall benefit is small due to the significant adverse effects associated with the systemic therapy. Paclitaxel is one of the most widely used chemotherapeutic agents, often utilized as a first-line therapy for breast, ovarian, and non-small cell lung cancers. The poor aqueous solubility of paclitaxel requires formulation with a mixture of Cremophor EL and ethanol for intravenous delivery, but acute hypersensitivity reactions (41%) and nerve damage (60%) leading to abnormal sensation and pain in the extremities, significantly limit clinical effectiveness. Other common side effects due to systemic administration include low blood counts (70-90% of patients) with the resultant risk of infection, hair loss (87%), decreased oxygen exchange, fatigue or muscle/bone pain (60%), nausea and vomiting (52%), diarrhea (38%), mouth sores (31%) and bleeding (14%).

Localized drug delivery has been identified as a preferred mode of treatment for a number of medical conditions including but not limited atherosclerosis (stents) and control of inflammation/wound healing. In particular, localized drug delivery is an attractive and actively investigated medium for the treatment of most localized forms of cancer. Drugs, contrast agents, and targeting moieties have been covalently-bound or entrapped by a polymer in the form of prodrugs, micelles, particles, or bulk material in an attempt to both increase solubility and localize delivery to tumors via systemic targeting or local delivery. A drug delivery platform that locally delivers therapeutic doses of drug directly to the site of disease, while also significantly diminishing the systemic toxicity associated with intravenous chemotherapy and external radiation, offers significant advantages over all currently available approaches to prevent local tumor growth or recurrence. Loco-regional delivery is particularly beneficial in situations where: 1) therapeutic levels of chemotherapy are not achievable due to poor aqueous solubility, non-ideal pharmacokinetics or biodistribution, 2) systemic treatment approaches are ineffective or highly toxic, 3) the incidence of local recurrence does not warrant universal treatment of all patients with a highly morbid systemic therapy, or 4) surgical resection of recurrent disease is not an option and alternative rescue therapies are generally unsuccessful.

A drug delivery device intended to prevent local recurrence must be localized to the resection margin and deliver chemotherapy directly to the site of potential recurrent disease. Ideally, the delivery platform will: (1) preserve the activity of the embedded drug molecules over the therapeutic lifetime; (2) release drug in a controlled and sustained manner to ensure adequate diffusion and uptake into cancer cells; (3) kill microscopic malignant disease in the local environment of the resection margins; (4) invoke minimal damage to healthy tissue; (5) eliminate side effects due to systemic circulation of the chemotherapeutic drug; and (6) be biocompatible. The delivery platform must ultimately reduce or eliminate the incidence of microscopic malignant disease at or near the site of resection, while preserving surrounding healthy lung tissue. Notably, both the choice of polymer and drug can profoundly affect release behavior through variations in thermal properties, relative crystallinity, and hydrophobicity of the polymer and partition coefficient, molecular weight, and loading of the drug.

Today, there are few delivery devices reported for the prevention of local growth of early or residual cancer. First, paclitaxel-loaded thermosensitive chitosan-based hydrogels, developed by Leroux et. al., were implanted four days after tumor cell inoculation and demonstrated a significant decrease, but not complete inhibition, of tumor growth. Second, Matsuda et. al. created a polyurethane-based pouch which was sutured subcutaneously in tumor-bearing mice and loaded with gemcitabine three days after tumor inoculation. Four of six mice supporting loaded devices had no observable tumor mass during the 30 day observation period, but the remaining two mice developed tumors at a rate comparable to the control mice. Third, cross-linked chitosan hydrogels have also been loaded with a radioisotope to deliver localized radiotherapy for prevention of tumor recurrence in breast cancer. Implants loaded with $^{131}$I-norcholesterol were co-implanted with 4T1 metastatic mammary mouse tumor cells to simulate microscopic residual disease and tumor growth was prevented in 69% of the mice.

The most established local chemotherapy delivery device to date is used in the treatment of malignant glioma, an aggressive brain cancer that often recurs near the resection margins of the primary, tumor. Commercially manufactured by MGI Pharma under the brand name GLIADEL®, the device delivers the chemotherapeutic carmustine from a rigid biodegradable polyanhydride wafer placed near the resection margins. The wafers have a modest impact on the survival of treated patients, but patients report a markedly higher quality of life compared to those treated by conventional systemic chemotherapy.

Although all of these materials are suitable for the delivery of anticancer agents locally, there is an absence of delivery systems that can be attached directly to tissue surfaces for prolonged periods of drug release. Hydrogel-based systems have been developed that are elastic in nature and adhere directly to tissues, but these materials release most of their loaded drug over a short duration, from hours to a couple days, and generally degrade or swell in the short term. The GLIADEL® wafer is a polymer matrix that is directly deposited in the resection cavity following surgical treatment of malignant glioma, and also releases the majority of its loaded drug over several days. Drug-eluting stents are effective at delivering anti-proliferative agents for days to weeks, and they remain fixed in place to treat diseased tissue locally, but they are not designed to be compliant to a range of tissue shapes and surfaces.

SUMMARY

A drug delivery system that includes a composite of a structural scaffolding material and a drug-eluting material that together can be attached to compliant tissue surfaces is disclosed, along with methods for constructing and applying these composites. In some embodiments, the present invention provides composites for delivery of a bioactive agent, including a scaffolding material and one or more polymer coatings, wherein at least one polymer coating includes one or more independently selected bioactive agents. In some embodiments, the present invention provides a compliant composite for delivery of a bioactive agent, comprising a scaffolding material, at least one polymer coating comprising one or more independently selected bioactive agents, and a bather layer positioned between said scaffolding material and the polymer coating. In some embodiments, the composite comprises multiple polymer coatings which may be positioned on top of the polymer coating containing the bio active agent(s) or between the barrier layer and the polymer coating containing the bioactive agent(s). Alternatively, the bioactive agent(s) may be present in multiple polymer coatings. In some embodiments, the composite is compliant.

In some embodiments, the scaffolding material is biocompatible and compliant to tissue. The scaffold and composite can be sterilized using e-beam or gamma treatment. In some embodiments, the scaffolding material is capable of conforming to tissue surfaces. The drug-eluting material should securely adhere to the scaffolding material over the intended length of treatment, i.e., the material should not significantly degrade and should remain attached to the scaffolding material as long as the drug-eluting material is releasing its drug. In some embodiments, the drug-eluting material will be a biocompatible and biodegradable polymer capable of controlled drug release, defined as continuous release of drug over hours, days, or weeks in a consistent and predictable manner. The composite should be able to tolerate common methods of application to tissue including surgical stapling, suturing, or adherence without disrupting or altering the drug release kinetics from the drug-eluting material or compromising the mechanical integrity of the composite as a whole.

In another aspect, the present invention further provides methods for preparing the composites of the invention, comprising the steps of:

(a) optionally, forming a barrier layer on the surface of the scaffolding layer; the forming of the barrier layer comprising coating the scaffolding material with a solution comprising one or more polymers and at least one solvent;

(b) forming a first polymer coating; wherein the forming of the first polymer coating comprises coating the scaffolding material or, if present, the optional bather layer, with a solution comprising one or more polymers and at least one solvent;

(c) optionally, forming one or more additional polymer coatings;

wherein at least one polymer coating comprises one or more independently selected bioactive agents.

In a further aspect, the present invention provides methods for preparing the composites of the invention, comprising the steps of:

(a) forming a barrier layer on the surface of the scaffolding layer; the forming of the barrier layer comprising coating the scaffolding material with a solution comprising one or more polymers and at least one solvent;

(b) forming a first polymer coating; wherein the forming of the first polymer coating comprises coating the barrier layer, with a solution comprising one or more polymers and at least one solvent;

(c) optionally, forming one or more additional polymer coatings;

wherein at least one polymer coating comprises one or more independently selected bioactive agents.

In some embodiments, a drug-loaded polymer coating is applied to a scaffolding material by premixing the polymer with drug in an organic solvent and casting the solution on the surface of the scaffold. In some embodiments, a scaffolding material is a material that is clinically used as a buttressing material to add mechanical integrity to weak tissue or to prevent fluid leaks such as blood or air. The drug-loaded coating should not interfere with the attachment of the scaffolding material to the tissue. In some embodiments, the composite has a normal compliance ratio to the tissue ranging of greater than one.

In some embodiments, one or more polymer layers of similar or different compositions than the drug-eluting layer will be adhered onto the scaffold before the drug-eluting layer to provide a barrier blocking release of drug towards the direction of the scaffold and/or to facilitate adherence of the drug-eluting polymer to the scaffold. The "barrier layer" not only promotes adhesion, but also creates a smooth surface over the scaffolding material that otherwise can be patterned or irregular, i.e., a woven fiber scaffold, and thus promotes a more even and consistent drug-eluting polymer coating when cast on top of the barrier layer. Strong adhesion is obtained between the layers and scaffold and reproducible drug release kinetics are achieved. The whole composite does not delaminate or otherwise mechanically fail when stapled with rows of small staples using a standard surgical stapler, or when sutured directly to tissue. The composite is particularly suited for the delivery of a therapeutic directly to the surface of a tissue for a prolonged duration, i.e., days to weeks. In some embodiments, the composite is fixated at the surface of surgical resection margins following the excision of a solid tumor. In some embodiments, the barrier layer does not comprise a bioactive agent.

In yet another aspect, the present invention provides methods of administering one or more bioactive agents to a patient in need thereof, by implanting the composites of the invention in the patient, generally near the site of the disease.

In an additional aspect, the present invention further provides methods of administering localized chemotherapeutic treatment to a patient in need thereof, by implanting the composites in the patient, wherein at least one of the one or more independently selected bioactive agents is a chemotherapeutic agent.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

DETAILED DESCRIPTION

Figure 1:
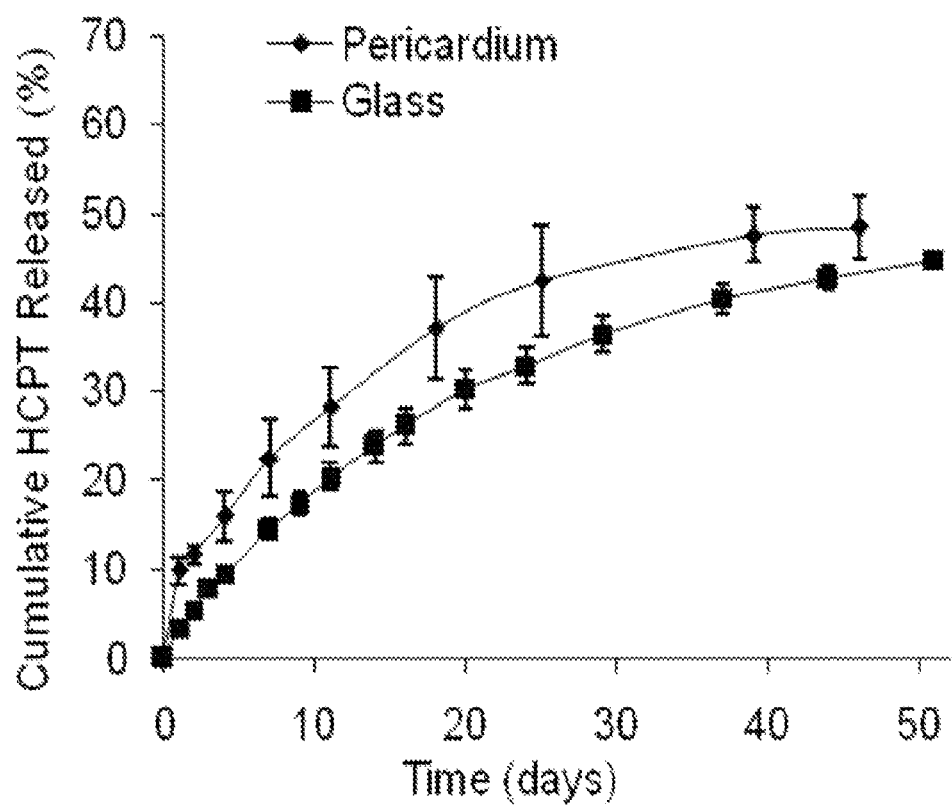
FIG. 1 is a graph that depicts the release of HCPT-loaded poly(glycerol monostearate-co-ε-caprolactone) films off glass or collagen-based scaffolds (N=3).
Figure 2:
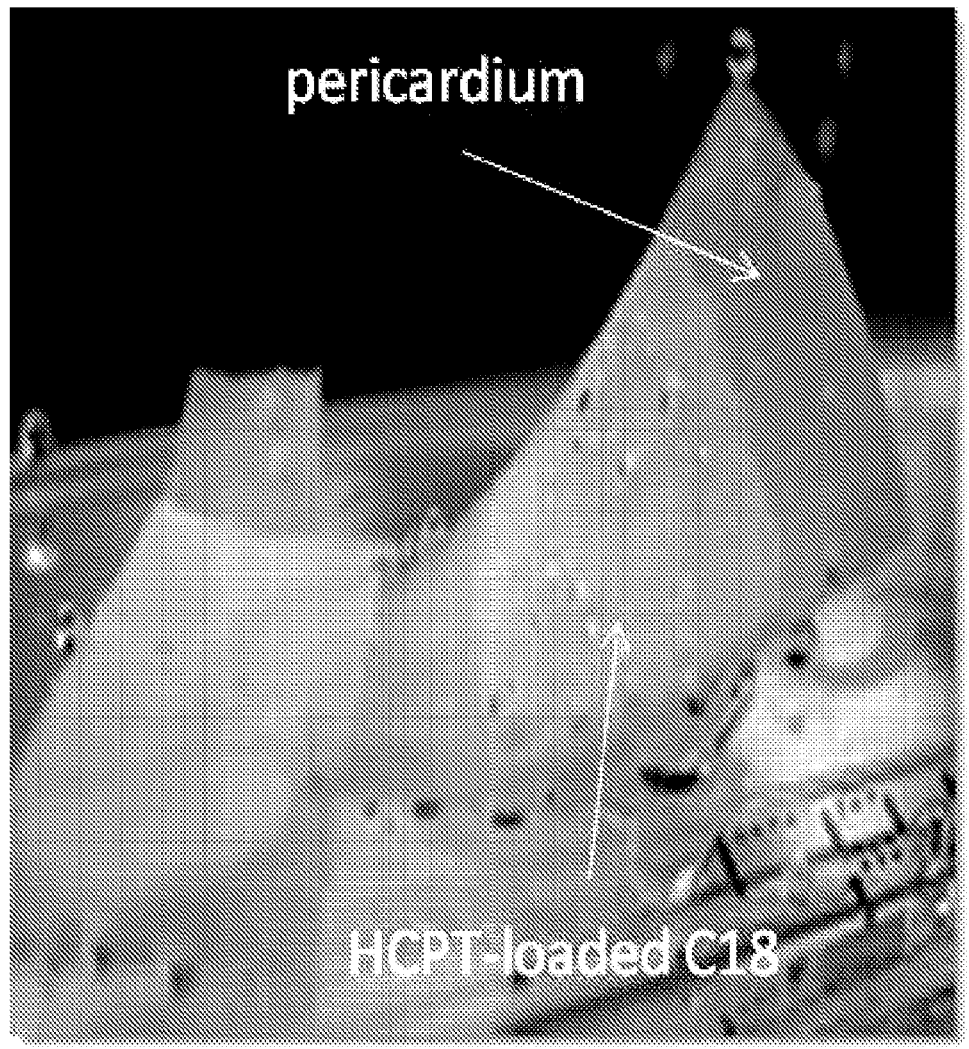
FIG. 2 is a photograph of film adhered to pericardium while submerged in phosphate buffered solution after 7 days.
Figure 3:
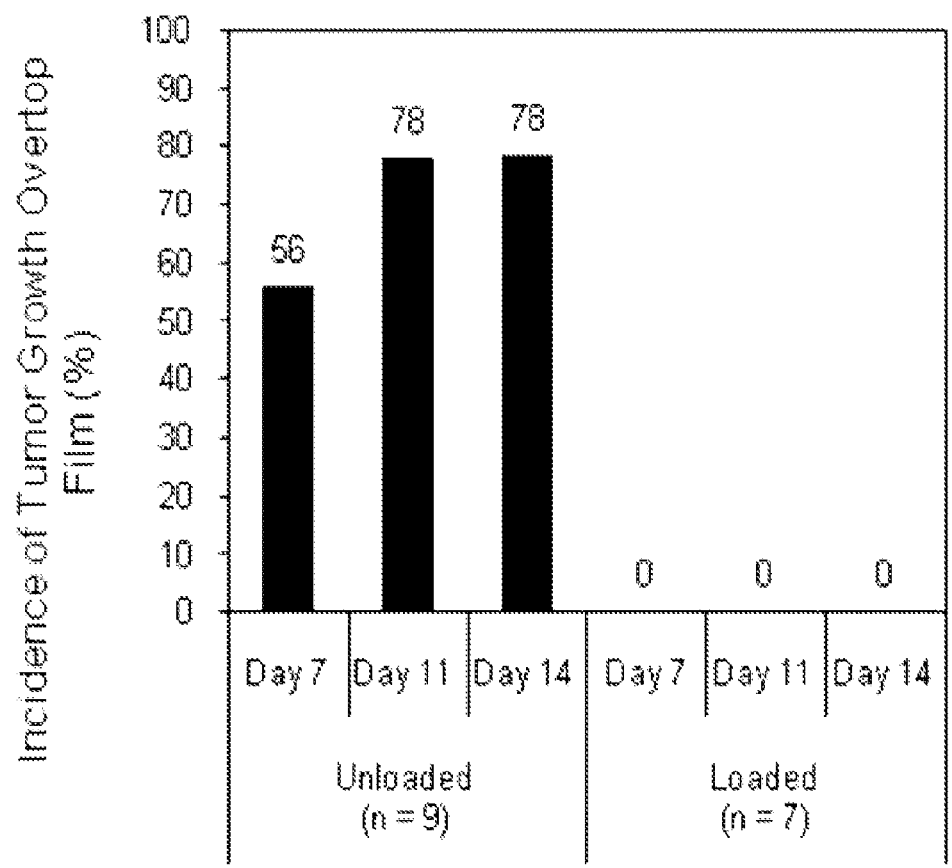
FIG. 3 is a bar graph that depicts the percentage of mice with local tumor growth within 0.5 cm of composites implanted subcutaneously. Some mice were euthanized before day 14 due to excessive tumor mass.
Figure 4:
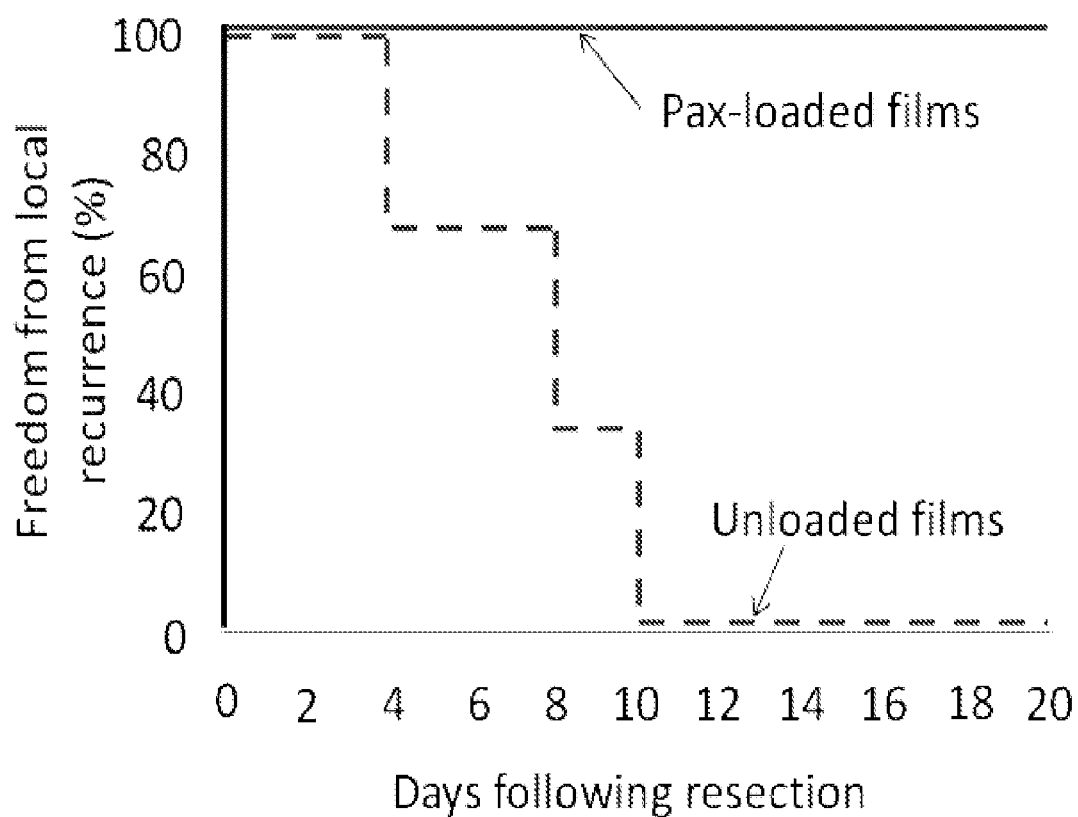
FIG. 4 is a graph that depicts the percentage of mice with local recurrent tumor growth following surgical resection.
Figure 5:
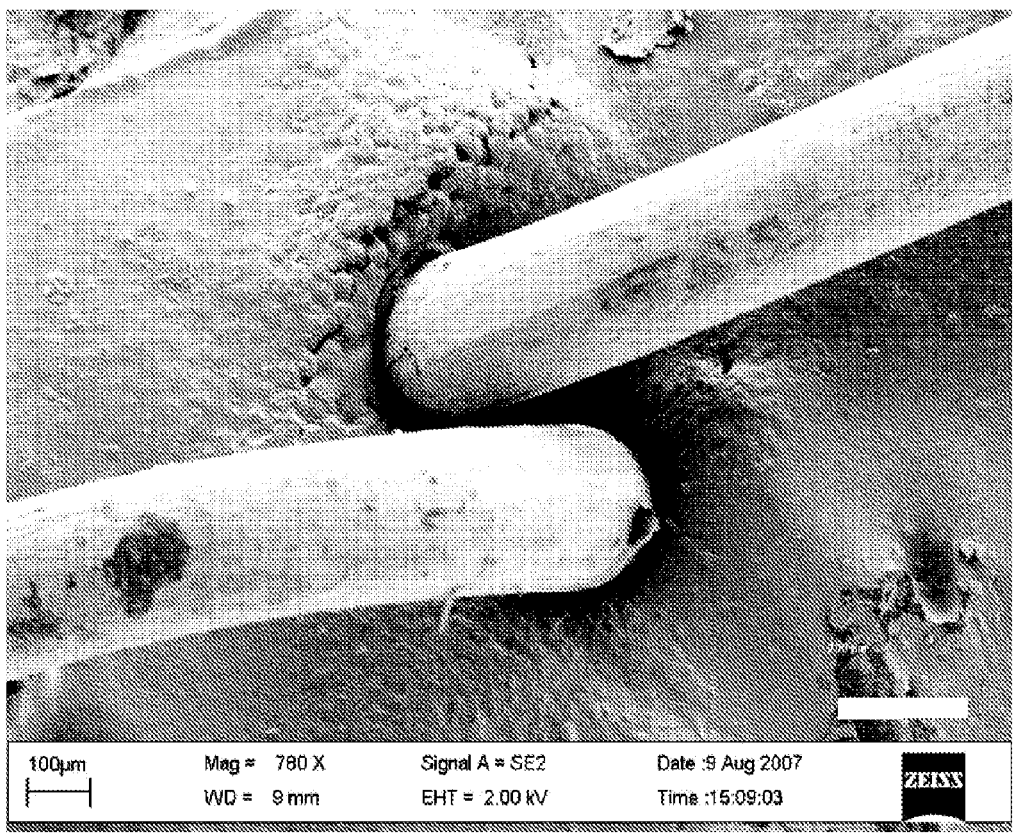
FIG. 5 is a SEM micrograph of a 10-hydroxycamptothecin-loaded composite stapled using a surgical stapler after 7 days in PBS at 37° C.

One method of increasing the exposure of surgical resection margins to drugs following the excision of a solid tumor is to deliver the drugs at the surface of the resection margins. Local delivery of chemotherapeutic drugs at the resection margins allows for continuous and concentrated levels of drug to be delivered at the site of tissue at highest risk for recurrence while minimizing the systemic side effects characteristic of traditional intravenous therapy. Such a treatment would especially benefit those cases where the incidence of local recurrence does not warrant universal treatment of all patients with a highly morbid systemic therapy. Biodegradable polymer devices including polymer rods, microparticles, and wafers, have been and are being developed to deliver drugs locally to solid tumors or within the resection tumor cavity for a prolonged duration.

As described herein, novel compliant composites capable of controlled delivery of therapeutic agents to tissue surfaces, material composition, and methods for manufacturing and administration to tissue are provided. In some embodiments, materials can be used which are described in PCT/US2007/070159, filed on May 13, 2007 (WO2007/140483, published on Dec. 16, 2007; also published as U.S. Patent Publ. No. 20080075718 (Ser. No. 11/756,587, filed May 31, 2007), the disclosure of which is incorporated herein by reference.

Definitions

As used herein, the term "biodegradable" refers to the erosion or degradation of a material into smaller entities which will be metabolized or excreted under the conditions normally present in a living tissue. Biodegradation is preferably predictable both in terms of the degradation products formed, including metabolic byproducts formed, and in terms of duration, whereas the duration of biodegradation can be dependant upon the chemical structure of the material.

As used herein, the term "biocompatible" refers to the absence of an adverse acute, chronic, or escalating biological response to an implant or coating, and is distinguished from a mild, transient inflammation which typically accompanies surgery or implantation of foreign objects into a living organism.

As used herein, the term "scaffold" refers to a material that provides a supporting framework to the overall composite. In some embodiments, the scaffold is a thin flexible material that is biocompatible and can be fixated to the surface of a tissue.

As used herein, the terms "barrier" or "barrier material" refers to a material that either enhances adhesion between two other materials, for example, a scaffold and a drug-loaded polymer, and/or a material that acts as a diffusion barrier, preferably to therapeutic agents released by a component of the composite.

As used herein, the terms "controlled release," "sustained release," and "prolonged release" refer to the continuous release of drugs from a material for at least 24 hours. In some embodiments, the continuous release is greater than 30 days. In some embodiments, the release kinetics are linear and repeatable.

As used herein, the term "compliance" or "compliant" is used in a general sense and refers for example to the ability of an implant to closely match the mechanical properties of tissues at the implant site, such as in the sense of bending or flexing with the natural movement of tissues at the implant site, except when "compliance" is used in the specific technical sense as the reciprocal of modulus.

As used herein, the term "normalized compliance" as applied to a thin flat sheet or film refers to strain divided by the applied stress, or force per cross-sectional area, divided by the thickness, thus for a sample with strain S, force F, width W, and thickness T, the normalized compliance is $NC=(S/(F/(W*T))/T$, or $S/(F/W)$. The normalized compliance allows direct comparison of the forces required to deform a material, for example the composite and tissue, without regard for thickness.

As used herein, the term "normalized compliance ratio" refers to the ratio of normalized compliance between the tissue and implant. When both measurements are conducted on strips of the same width and applied force, the ratio becomes the ratio of the two strains at a given force. A normalized compliance ratio that is greater than one implies the tissue is easier to deform than the implant, whereas a ratio smaller than one implies the implant is easier to deform than the tissue.

In some embodiments, the term "about" means plus or minus 10% of the value.

In some embodiments, the normalized compliance ratio for the composite is greater than about 1 to about 10,000, greater than about 1 to about 9,000, greater than about 1 to about 8 k, greater than about 1 to about 7,000, greater than about 1 to about 6,000, greater than about 1 to about 5,000, greater than about 1 to about 4,000, greater than about 1 to about 3,000, greater than about 1 to about 2,000, greater than about 1 to about 1,000, greater than about 1 to about 500, greater than about 1 to about 400, greater than about 1 to about 300, greater than about 1 to about 200, greater than about 1 to about 100, greater than about 1 to about 50, greater than about 1 to about 25, or greater than about 1 to about 10.

In some embodiments, the normalized compliance ratio for the composite is from about 10 to about 10,000, about 100 to about 10,000, about 200 to about 10,000, about 300 to about 10,000, about 400 to about 10,000, about 500 to about 10,000, or about 1,000 to about 10,000.

In some embodiments, the normalized compliance ratio for the composite is about from about 2,000 to about 10,000, about 2,000 to about 9,000, about 3,000 to about 9,000, about 3,000 to about 8,000, or about 4,000 to about 8,000.

In some embodiments, the normalized compliance ratio for the composite is about 8,000 to about 10,000, about 10,000 to about 15,000, or about 8,000 to about 15,000.

In some embodiments, the thickness of the barrier layer is from about 1 µm to about 2 mm, about 5 µm to about 2 mm, about 10 µm to about 2 mm, about 20 µm to about 0.5 mm, about 5 µm to about 2 mm, about 5 µm to about 1 mm, about 5 µm to about 0.5 mm, about 5 µm to about 500 µm, about 5 µm to about 400 µm, about 5 µm to about 300 µm, about 5 µm to about 200 µm, about 5 µm to about 100 µm, about 5 µm to about 90 µm, about 10 µm to about 90 µm, about 10 µm to about 80 µm, about 20 µm to about 80 µm, or about 30 µm to about 80 µm. In some embodiments, the thickness of the barrier layer is about 50 µm.

As used herein, the terms "treating" or "treatment" encompass either or both responsive and prophylaxis measures, e.g., designed to inhibit, slow, or delay the onset of a symptom of a disease or disorder, achieve a full or partial reduction of a symptom or disease state, and/or to alleviate, ameliorate, lessen, or cure a disease or disorder and/or its symptoms.

As used herein, amelioration of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

As used herein, the term "subject" is a human or an animal, typically a mammal, such as a cow, horse, dog, cat, pig, sheep, monkey, or other laboratory or domesticated animal. As used herein, the term "patient" includes human and animal subjects.

As used herein, the term "pharmaceutical composition" refers to a chemical compound or composition capable of inducing a desired therapeutic effect in a subject. In certain embodiments, a pharmaceutical composition contains an active agent, which is the agent that induces the desired therapeutic effect. The pharmaceutical composition can contain a prodrug of the compounds provided herein. In certain embodiments, a pharmaceutical composition contains inactive ingredients, such as, for example, carriers and excipients.

The phrase "therapeutically effective amount" refers to the amount of a pharmaceutical composition that elicits the biological or medicinal response in a tissue, system, animal, individual, patient, or human that is being sought by a researcher, veterinarian, medical doctor or other clinician.

As used herein, the term "pharmaceutically acceptable" refers to a formulation of a compound that does not significantly abrogate the biological activity, a pharmacological activity and/or other properties of the compound when the formulated compound is administered to a subject. In certain embodiments, a pharmaceutically acceptable formulation does not cause significant irritation to a subject.

As used herein, pharmaceutically acceptable derivatives of a compound include, but are not limited to, salts, esters, enol ethers, enol esters, acetals, ketals, orthoesters, hemiacetals, hemiketals, acids, bases, solvates, hydrates, PEGylation, or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to chloroprocaine, choline, N,N'-dibenzyl-ethylenediamine, ammonia, diethanolamine and other hydroxyalkylamines, ethylenediamine, N-methylglucamine, procaine, N-benzyl-phenethylamine, 1-para-chloro-benzyl-2-pyrrolidin-1'-ylmethyl-benzimidazole, diethylamine and other alkylamines, piperazine and tris(hydroxymethyl)-aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl, or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl, or heterocyclyl. Pharmaceutically acceptable solvates and hydrates are complexes of a compound with one or more solvent or water molecules, or 1 to about 100, or 1 to about 10, or one to about 2, 3, or 4, solvent or water molecules.

A "bioactive agent" refers to an agent that is capable of exerting a biological effect in vitro and/or in vivo. The biological effect can be therapeutic in nature. As used herein, "bioactive agent" refers also to a substance that is used in connection with an application that is diagnostic in nature, such as in methods for diagnosing the presence or absence of a disease in a patient. The bioactive agents can be neutral or positively or negatively charged. Examples of suitable bioactive agents include pharmaceuticals and drugs, cells, gases and gaseous precursors (e.g., $O_2$), synthetic organic molecules, proteins, enzymes, growth factors, vitamins, steroids, polyanions, nucleosides, nucleotides, polynucleotides, and diagnostic agents, such as contrast agents for use in connection with magnetic resonance imaging, ultrasound, positron emission transmography, computed tomography, or other imaging modality of a patient.

Scaffolds, which may be used with the composite according to the present invention, include commercially available products. Examples of film and mesh scaffold into which a fibrosis-inducing agent can be incorporated include INTERCEED (Johnson & Johnson, Inc.), PRECLUDE (W.L. Gore), and POLYACTIVE (poly(ether ester) multiblock copolymers (Osteotech, Inc., Shrewsbury, N.J.), based on poly(ethylene glycol) and poly(butylene terephthalate), and SURGICAL absorbable hemostat gauze-like sheet from Johnson & Johnson. Another mesh is a prosthetic polypropylene mesh with a bioresorbable coating called SEPRAMESH Biosurgical Composite (Genzyme Corporation, Cambridge, Mass.). One side of the mesh is coated with a bioresorbable layer of sodium hyaluronate and carboxymethylcellulose, providing a temporary physical barrier that separates the underlying tissue and organ surfaces from the mesh. The other side of the mesh is uncoated, allowing for complete tissue ingrowth similar to bare polypropylene mesh. In one embodiment, the fibrosis-inducing agent may be applied only to the uncoated side of SEPRAMESH and not to the sodium hyaluronate/carboxymethylcellulose coated side. Other films and meshes include: (a) BARD MARLEX mesh (C.R. Bard, Inc.), which is a very dense knitted fabric structure with, low porosity; (b) monofilament polypropylene mesh such as PROLENE available from Ethicon, Inc. Somerville, N.J. (see, e.g., U.S. Pat. Nos. 5,634,931 and 5,824,082)); (c) SURGISIS GOLD and SURGISIS IHM soft, tissue graft (both from Cook Surgical, Inc.) which are devices specifically configured for use to reinforce soft tissue in repair of inguinal hernias in open and laparoscopic procedures; (d) thin walled polypropylene surgical meshes such as are available from Atrium Medical Corporation (Hudson, N.H.) under the trade names PROLITE, PROLITE ULTRA, and LITEMESH; (e) COMPOSIX hernia mesh (C.R. Bard, Murray Hill, N.J.), which incorporates a mesh patch (the patch includes two layers of an inert synthetic mesh, generally made of polypropylene, and is described in U.S. Pat. No. 6,280,453) that includes a filament to stiffen and maintain the device in a flat configuration; (f) VISILEX mesh (from C.R. Bard, Inc.), which is a polypropylene mesh that is constructed with monofilament polypropylene; (g) other meshes available from C.R. Bard, Inc. which include PERFIX Plug, KUGEL Hernia Patch, 3D MAX mesh, LHI mesh, DULEX mesh, and the VENTRALEX Hernia Patch; and (h) other types of polypropylene monofilament hernia mesh and plug products include HERTRA mesh 1, 2, and 2A, HERMESH 3, 4 & 5 and HERNIAMESH plugs T1, T2, and T3 from Herniamesh USA, Inc. (Great Neck, N.Y.).

Where reference is made to a URL or other such identifier or address, it understood that such identifiers can change and particular information on the internet can come and go, but equivalent information can be found by searching the internet. Reference thereto evidences the availability and public dissemination of such information.

Composite Formulation and Preparation

A scaffolding material is used as a supporting framework for a drug-loaded material to provide mechanical strength, flexibility, and/or to facilitate prolonged attachment to the site of disease of compliant tissue. In some embodiments, the scaffolding material will be biocompatible, biodegradable, and composed of natural or synthetic polymers capable of conforming to irregular tissue surfaces. The scaffolding material should be relatively thin compared to the tissue, and meet the appropriate mechanical requirements, such as compliance, which can be achieved, but is not limited to the selection of compliant polymers, or the processing of otherwise rigid polymers into a flexible state, i.e., a knitted or woven network of fibers like that found in. Dacron® vascular prostheses. In some embodiments, the scaffolding material will be pericardium or PTFE staple line reinforcement strips indicated for but not limited to bariatric and thoracic procedures. Reinforcement strips are clinically utilized as buttressing materials after surgical resection to prevent tears or leaks in weakened tissue at or near the resection margins. Scaffolding materials are usually stapled into place using a surgical stapler that simultaneous cuts as it staples, or the materials are sutured into place. A scaffold material can be administered to tissue in any manner that ensures the scaffold is fixated in place.

In some embodiments, the scaffolding material and the polymer layer are each biocompatible and biodegradable. In some embodiments, the scaffolding material comprises one or more materials independently selected from the group consisting of a polyester, a polycarbonate, a polyamide, a polyether, a polyanhydride, a copolymer thereof, collagen, modified collagen, hylauronic acid, and a natural polymer. In some embodiments, the scaffolding material comprises one or more materials independently selected from the group consisting of polyester, a polycarbonate, a polyamide, a polyether, a polyanhydride, a copolymer thereof, collagen, modified collagen, hylauronic acid, PTFE, poly(fluorocarbons), and a natural polymer In some embodiments, the scaffolding material is collagen.

In some embodiments, the normalized compliance ratio of tissue to composite is greater than one. In some embodiments, the scaffolding material is a buttressing material. In some embodiments, the normalized compliance ratio of tissue to composite is from about 0.05 to about 5000.

The drug-eluting polymer coatings should securely adhere to the scaffolding material over the intended length of treatment, i.e., the material should not significantly degrade and should remain attached to the scaffolding material as long as the drug-eluting material is releasing its drug. In some embodiments, the drug-eluting material will be a biocompatible and biodegradable polymer capable of controlled drug release, defined as continuous release of drug over hours, days, or weeks in a consistent and predictable manner. In some embodiments, the drug-eluting material will be comprised of polylactide, polyglycolide, polycaprolactone, poly (glycerol carbonate), or copolymers thereof or other polyester, polycarbonate, polyamide, polyether, polyanhydride, or copolymers thereof and loaded with one or more anticancer agents such as paclitaxel, pemetrexed, or members from the camptothecin family. The composite should be able to tolerate common methods of application to tissue including surgical stapling, suturing, or adherence without disrupting or altering the drug release kinetics from the drug-eluting material or compromising the mechanical integrity of the composite as a whole.

In some embodiments, the polymer coating, or multiple polymer coatings, each comprise one or more polymers independently selected from the group consisting of a polyester, a polycarbonate, a polyamide, a polyether, a polyanhydride, and a copolymer thereof. In some embodiments, the polymer coating, or multiple polymer coatings, each comprise one or more polymers independently selected from the group consisting of poly(caprolactone), poly(lactide-co-glycolide), and poly(glycerol monostearate-co-caprolactone). In some embodiments, polymer coating, or multiple polymer coatings, each comprise one or more polymers independently selected from the group consisting of poly(lactide-co-glycolide) and poly(glycerol monostearate-co-caprolactone). In some embodiments, at least one of the polymer coatings is a hydrogel.

In some embodiments, at least one of the polymer coatings is an oligomer or polymer, or portion thereof, represented by Formula XXXVIII:

XXXVIII

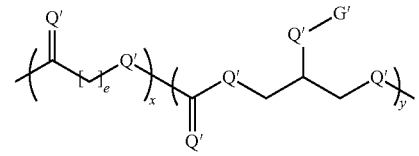

wherein:
each Q' is independently selected from O, S, Se, and NH;
G' is selected from

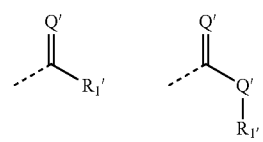

and $R_1'$;

R$_1$' is selected a straight or branched alkyl, cycloalkyl, aryl, olefin, silyl, alkylsilyl, arylsilyl, alkylaryl, arylalkyl, and fluorocarbon chain of 3-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or R$_1$' is selected from poly(ethylene glycol), poly(ethylene oxide), poly(hydroxyacid)); a carbohydrate, a protein, a polypeptide, an amino acid, a nucleic acid, a nucleotide, a polynucleotide, any DNA or RNA segment, a lipid, a polysaccharide, an antibody, a pharmaceutical agent, and any epitope for a biological receptor; or, R$_1$' is selected from a photocrosslinkable and ionically crosslinkable group;

x and y are each independently selected from an integer of 2-750;

e is selected from an integer of 1-8; and each polymeric terminal group is selected from amines, thiols, amides, phosphates, sulphates, hydroxides, metals, alkanes, alkenes and alkynes.

Methods of making the oligomers and polymers of Formula XXXVIII, and embodiments thereof, are described in PCT/US2007/070159, filed on May 13, 2007 (WO2007/140483, published on Dec. 16, 2007; also published as U.S. Patent Publ. No. 20080075718 (Ser. No. 11/756,587, filed May 31, 2007), each of which is incorporated by reference in its entirety.

In some embodiments, R$_1$' is selected from a straight or branched alkyl, cycloalkyl, aryl, olefin, silyl, alkylsilyl, arylsilyl, alkylaryl, arylalkyl, and fluorocarbon chain of 3-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents. In some embodiments, R$_1$' is selected from a straight or branched alkyl, cycloalkyl, aryl, olefin, silyl, alkylsilyl, arylsilyl, alkylaryl, arylalkyl, and fluorocarbon chain of 3-50 carbons. In some embodiments, R$_1$' is selected from a straight or branched alkyl chain of 3-50 carbons.

In some embodiments, G' is —C(=O)R$_1$'; and each Q' is O.

In certain embodiments, R$_1$' is selected from:

methyl ethyl isopropyl

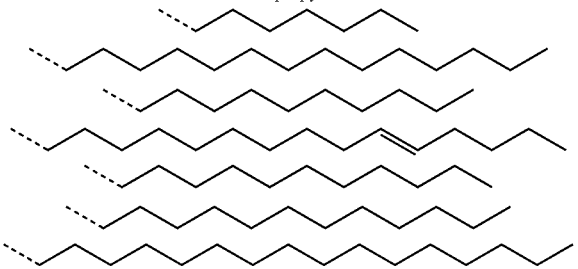

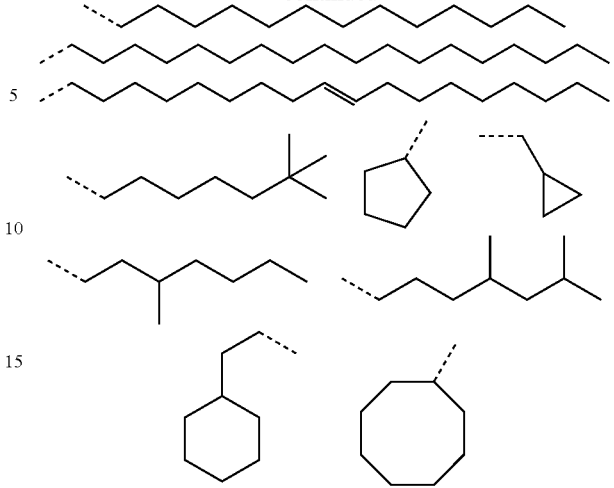

"Alkyl", as used alone or in combination with other terms, refers to an aliphatic hydrocarbon group which can be straight or branched having 1 to about 60 carbon atoms in the chain, and which preferably have about 6 to about 50 carbons in the chain. "Lower alkyl" refers to an alkyl group having 1 to about 8 carbon atoms. "Higher alkyl" refers to an alkyl group having about 10 to about 20 carbon atoms. The alkyl group can be optionally substituted with one or more alkyl group substituents which can be the same or different, where "alkyl group substituent" includes halo, amino, aryl, hydroxy, alkoxy, aryloxy, alkyloxy, alkylthio, arylthio, aralkyloxy, aralkylthio, carboxy, alkoxycarbonyl, oxo and cycloalkyl. There can be optionally inserted along the alkyl chain one or more oxygen, silicon, sulfur, or substituted or unsubstituted nitrogen atoms, wherein the nitrogen substituent is lower alkyl. "Branched" refers to an alkyl group in which a lower alkyl group, such as methyl, ethyl, or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl. Useful alkyl groups include branched or straight chain alkyl groups of 6 to 50 carbon, and also include the lower alkyl groups of 1 to about 4 carbons and the higher alkyl groups of about 12 to about 16 carbons.

"Alkenyl" refers to an alkyl group containing at least one carbon-carbon double bond. The alkenyl group can be optionally substituted with one or more "alkyl group substituents." Exemplary alkenyl groups include vinyl, allyl, n-pentenyl, decenyl, dodecenyl, tetradecadienyl, heptadec-8-en-1-yl and heptadec-8,11-dien-1-yl.

"Alkynyl" refers to an alkyl group containing a carbon-carbon triple bond. The alkynyl group can be optionally substituted with one or more "alkyl group substituents."Exemplary alkynyl groups include ethynyl, propargyl, n-pentynyl, decynyl, and dodecynyl. Useful alkynyl groups include the lower alkynyl groups.

"Cycloalkyl" refers to a non-aromatic mono- or multicyclic ring system of about 4 to about 10 carbon atoms. The cycloalkyl group can be optionally partially unsaturated. The cycloalkyl group can be also optionally substituted with an aryl group substituent, oxo and/or alkylene. Representative monocyclic cycloalkyl rings include cyclopentyl, cyclohexyl, and cycloheptyl. Useful multicyclic cycloalkyl rings include adamantyl, octahydronaphthyl, decalin, camphor, camphane, and noradamantyl.

"Aryl" refers to an aromatic carbocyclic radical containing about 6 to about 10 carbon atoms. The aryl group can be optionally substituted with one or more aryl group substituents, which can be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, rylthio, alkylthio, alkylene, and —NRR', where R and R' are each independently hydrogen, alkyl, aryl, and aralkyl. Exemplary aryl groups include substituted or unsubstituted phenyl and substituted or unsubstituted naphthyl.

"Acyl" refers to an alkyl-CO— group, wherein alkyl is as previously described. Exemplary acyl groups comprise alkyl of 1 to about 30 carbon atoms. Exemplary acyl groups also include acetyl, propanoyl, 2-methylpropanoyl, butanoyl, and palmitoyl.

"Aroyl" means an aryl-CO— group, wherein aryl is as previously described. Exemplary aroyl groups include benzoyl, and 1- and 2-naphthoyl.

"Alkoxy" refers to an alkyl-O— group, wherein alkyl is as previously described. Exemplary alkoxy groups include methoxy, ethoxy, n-propoxy, i-propoxy, n-butoxy, and heptoxy.

"Aryloxy" refers to an aryl-O— group, wherein the aryl group is as previously described. Exemplary aryloxy groups include phenoxy and naphthoxy.

"Alkylthio" refers to an alkyl-S— group, wherein alkyl is as previously described. Exemplary alkylthio groups include methylthio, ethylthio, i-propylthio, and heptylthio.

"Arylthio" refers to an aryl-S— group, wherein the aryl group is as previously described; Exemplary arylthio groups include phenylthio and naphthylthio.

"Aralkyl" refers to an aryl-alkyl- group, wherein aryl and alkyl are as previously described. Exemplary aralkyl groups include benzyl, phenylethyl, and naphthylmethyl.

"Aralkyloxy" refers to an aralkyl-O— group, wherein the aralkyl group is as previously described. An exemplary aralkyloxy group is benzyloxy.

"Aralkylthio" refers to an aralkyl-S— group, wherein the aralkyl group is as previously described. An exemplary aralkylthio group is benzylthio.

"Dialkylamino" refers to an —NRR' group, wherein each of R and R' is independently an alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group, wherein one of R and R' is hydrogen and the other of R and R' is alkyl as previously described.

"Dialkylcarbamoyl" refers to R'RN—CO— group, wherein each of R and R' is independently alkyl as previously described.

"Acyloxy" refers to an acyl-O— group, wherein acyl is as previously described.

"Acylamino" refers to an acyl-NH— group, wherein acyl is as previously described.

"Aroylamino" refers to an aroyl-NH— group, wherein aroyl is as previously described.

"Alkylene" refers to a straight or branched bivalent aliphatic hydrocarbon group having from 1 to about 30 carbon atoms. The alkylene group can be straight, branched, or cyclic. The alkylene group can be also optionally unsaturated and/or substituted with one or more "alkyl group substituents." There can be optionally inserted along the alkylene group one or more oxygen, sulphur, or substituted or unsubstituted nitrogen atoms, wherein the nitrogen substituent is alkyl as previously described. Exemplary alkylene groups include methylene (—$CH_2$—), ethylene (—$CH_2$—$CH_2$—), propylene (—$(CH_2)_3$—), cyclohexylene (—$C_6H_{10}$—), —CH=CH—CH=CH—, —CH=CH—$CH_2$—, —$(CF_2)_n$$(CH_2)_m$—, wherein n is an integer from about 1 to about 50 and m is an integer from 0 to about 50, —$(CH_2)_n$—N(R)—$(CH_2)_m$—, wherein each of m and n is independently an integer from 0 to about 50 and R is hydrogen or alkyl, methylenedioxy (—O—$CH_2$—O—), and ethylenedioxy (—O—$(CH_2)_2$—O—). An alkylene group can have about 2 to about 3 carbon atoms and can further have 6-50 carbons.

A "barrier layer" can be necessary to serve as a diffusion barrier between the drug-eluting polymer and the scaffold, in effect directing drug release towards the tissue. The "barrier layer" can also be necessary to facilitate adherence or promote film formation between the scaffold and drug-eluting layer, particularly in instances where the polymer-drug solution cannot be readily cast on the surface of the scaffold due to permeability or surface compatibility issues between the two materials. In some embodiments, the "barrier layer" will be biocompatible and biodegradable, impede the diffusion of drug towards the scaffold, promote adherence between layers, and be relatively thin compared to the entire composite.

In some embodiments, the composite further comprises a barrier layer between the scaffolding material and the one or more polymer coatings. In some embodiments, the barrier layer comprises one or more independently selected materials that impede the release of the bioactive agent in the direction of the scaffolding material. In some embodiments, the barrier layer comprises one or more independently selected materials that facilitates adherence or film formation of the one or more polymer coatings on the scaffolding material. In some embodiments, the barrier layer comprises poly(lactide-glycolide), poly(trimethylene carbonate), poly(dioxanone), or poly(caprolactone). In some embodiments, the barrier layer comprises poly(caprolactone).

In some embodiments, the barrier layer inhibits diffusion of the bioactive agent(s) in the direction of the scaffolding material. In some embodiments, the ability of the barrier layer to impede diffusion of the bioactive agent(s) may be determining by measuring the diffusion of the bioactive agents(s) from the scaffolding side of the composite wherein the bioactive agent(s) comprising polymer coating is on the opposite side of the composite. In some embodiments, the diffusion is measured by first preparing a multilayer composite, with a barrier layer coated directly on the scaffolding material; and at least one additional polymer coating containing the desired bioactive agent. The scaffolding side of the composite is then exposed to a solution of PBS at 37° C. (see example 2). At specific time points; an aliquot of release media is removed and the concentration of the bio active agent is measured by an appropriate analytical technique. The percentage of bioactive agent in the composite released after 24 hours from the scaffolding side of the composite is then calculated. In some embodiments, the barrier layer allows less than about 20%, less than about 15%, less than about 10%, less than about 9%, less than about 8%, less than about 7%, less than about 6%, less than about 5%, less than about 4%, less than about 3%, less than about 2%, less than about 1%, less than about 0.5%, less than about 0.25%, or less than about 0.1% of the bioactive agent to be released from the scaffolding side of the composite in a 24 hour period.

The drug-eluting polymer and/or barrier layers can be applied to the scaffold in several ways including, but not limited to, solvent casting, compression molding, melting, or adhesion of polymer films or micro/nano-particles. In some embodiments, a barrier layer is solvent cast onto the scaffold followed by the casting of one or more drug-containing polymer layers. Various polymer-organic solvent mixtures can be used to apply each polymer layer without significantly dissolving the preceding layers. In the case of solvent casting, the drug(s) will be premixed with the polymer in an organic solvent. For drugs with low solubility in the hydrophobic organic solvent, the polymer-drug solution will be agitated, for example by sonication, to homogenous the drug crystals in solution. The drug(s) do not need to be completely soluble in solution to form drug-loaded polymers capable of controlled release.

These methods can be used to make slabs, sheets, films, strips, coatings, tubes, or other structures. In some embodiments, the composites are made into strips that can cover the surface of the diseased tissue.

In some embodiments, the present invention provides a method for preparing the composite, including the steps of:

(a) optionally, forming a barrier layer on the surface of the scaffolding layer; the forming of the barrier layer comprising coating the scaffolding material with a solution comprising one or more polymers and at least one solvent;

(b) forming a first polymer coating; wherein the forming of the first polymer coating comprises coating the scaffolding material or, if present, the optional barrier layer, with a solution comprising one or more polymers and at least one solvent;

(c) optionally, forming one or more additional polymer coatings;

wherein at least one polymer coating comprises one or more independently selected bioactive agents.

In some embodiments, the present invention provides a method for preparing the composite, including the steps of:

(a) forming a barrier layer on the surface of the scaffolding layer; the forming of the barrier layer comprising coating the scaffolding material with a solution comprising one or more polymers and at least one solvent;

(b) forming a first polymer coating; wherein the forming of the first polymer coating comprises coating the barrier layer, with a solution comprising one or more polymers and at least one solvent;

(c) optionally, forming one or more additional polymer coatings;

wherein at least one polymer coating comprises one or more independently selected bioactive agents.

In some embodiments, the present invention provides a composite for delivery of a bioactive agent, comprising a scaffolding material and one or more polymer coatings, wherein at least one of said one or more polymer coatings is both a barrier layer and a coating comprising one or more independently selected bioactive agents.

In some embodiments, each solution independently comprises ethanol, methanol, dichloromethane, tetrahydrofuran, chloroform, toluene, acetone, hexane, cyclohexane, ethyl acetate, isopropanol, pentane, acetonitrile, and combination thereof. In some embodiments, the solution of step (a) comprises one or more independently selected bioactive agents.

In some embodiments, the composite comprises multiple polymer coatings. In some embodiments, the composite comprises a barrier layer. In some embodiments, the barrier layer is cast from a solution comprised of an organic solvent and a biodegradable polymer, wherein the solution can be spread along the surface of the scaffold without significantly permeating the scaffolding material. In some embodiments, the one or more polymer layers are coated on one side of the scaffolding material.

The methods of preparation can be used to prepare any of the embodiments of the composites described herein, or combination thereof.

Bioactive Agents to be Encapsulated

The polymers provided herein can be used to deliver any agent. The agent can be in any pharmaceutically acceptable form, including pharmaceutically acceptable salts. A large number of pharmaceutical agents are known in the art and are amenable for use in the pharmaceutical compositions of the polymeric materials described herein. Acceptable agents include, but are not limited to, chemotherapeutic agents, such as radiosensitizers, receptor inhibitors and agonists or other anti-neoplastic agents; immune modulators and bioactive agents, such as cytokines, growth factors, or steroids with or without the co-incorporation of tumor or pathogen antigens to increase the anti-neoplastic response as a means of vaccine development; local anesthetic agents; antibiotics; or nucleic acids as a means of local gene therapy.

Any agent can be incorporated within the polymer films and particles described herein. For example, a polymer film or particle described herein can incorporate a pharmaceutical agent selected from among (1) nonsteroidal anti-inflammatory drugs (NSAIDs) analgesics, such as diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) H1—blocker antihistamines, such as clemastine and terfenadine; (5) H2—blocker antihistamines, such as cimetidine, famotidine, nizadine, and ranitidine; (6) anti-infective agents, such as mupirocin; (7) anti-anaerobic anti-infectives, such as chloramphenicol and clindamycin; (8) antifungal antibiotic anti-infectives, such as, amphotericin b, clotrimazole, fluconazole, and ketoconazole; (9) macrolide antibiotic anti-infectives, such as azithromycin and erythromycin; (10) miscellaneous beta-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alpha, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alpha, paclitaxel, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) alpha-blocker sympatholytics, such as prazosin; (34) beta-blocker sympatholytics, such as atenolol; (35) adrenergic agonist sympathomimetics, such as albuterol and dobutamine; (36) cardiovascular agents, such as aspirin (ASA), plavix (Clopidogrel bisulfate) etc; (37) beta-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I anti-arrhythmics, such as lidocaine, mexiletine, phenyloin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) alpha-blocker antihypertensives, such as prazosin; (46) angiotensin-converting enzyme inhibitor (ACE inhibitor) antihypertensives, such as captopril and enalapril; (47) beta blocker antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diurectic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as amrinone, dobutamine, and dopamine; (56) cardiac glycoside inotropes, such as digoxin; (57) thrombolytic agents or enzymes, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal topical antiinfectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as RNase and DNase; (69) immunosupressive agents, such as cyclosporine, steroids, methotrexate tacrolimus, sirolimus, rapamycin; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) $H_2$—blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic antianemia agents, such as erythropoietin, filgrastim (G-CSF), and sargramostim (GM-CSF); (78) coagulation agents, such as antihemophilic factors 1-10 (AHF 1-10); (79) anticoagulants, such as warfarin, heparin, and argatroban; (80) growth receptor inhibitors, such as erlotinib and gefetinib; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadatropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin 1M, IMIG, IGIM and immune globulin IV, NIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenyloin, and valproic acid; (103) barbiturate anticonvulsants, such as phenobarbital and primidone; (104) benzodiazepine anticonvulsants, such as clonazepam, diazepam, and lorazepam; (105) anti-parkisonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) beta-blocker anti-glaucoma agents, such as timolol; (110) miotic anti-glaucoma agents, such as pilocarpine; (111) ophthalmic aminoglycoside antiinfectives, such as gentamicin, neomycin; and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfuram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; (129) vitamin D compounds, such as calcitriol; (130) vitamin A, vitamin E, and vitamin E compounds; (131) poisons, such as racin; (132) anti-bleeding agents, such as protamine; (133) antihelminth anti-infectives, such as metronidazole; and (134) sclerosants such as talc, alcohol, and doxycyclin.

In addition to the foregoing, the following less common drugs can also be used: chlorhexidine; estradiol cypionate in oil; estradiol valerate in oil; flurbiprofen; flurbiprofen sodium; ivermectin; levodopa; nafarelin; and somatropin. Further, the following drugs can also be used: recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-1a; lenograstim (G-CSF); olanzapine; recombinant thyroid stimulating hormone (r-TSH); and topotecan. Further still, the following intravenous products can be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alpha; etoposide (VP-16); fluorouracil (5-FU); ganciclovir sodium; gentamicin sulfate; interferon alpha; leuprolide acetate; meperidine HCl; methadone HCl; methotrexate sodium; paclitaxel; ranitidine HCl; vinblastin sulfate; and zidovudine (AZT).

Further specific examples of useful pharmaceutical agents from the above categories include: (a) anti-neoplastics such as androgen inhibitors, antimetabolites, cytotoxic agents, receptor inhibitors, and immunomodulators; (b) anti-tussives such as dextromethorphan, dextromethorphan hydrobromide, noscapine, carbetapentane citrate, and chlorphedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines, and other bioactive peptidic compounds, such as interleukins 1-18 including mutants and analogues, RNase, DNase, luteinizing hormone releasing hormone (LHRH) and analogues, gonadotropin releasing hormone (GnRH), transforming growth factor-β. (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1-7 (BMP 1-7), somatostatin, thymosin-alpha-1, gamma-globulin, superoxide dismutase (SOD), complement factors, hGH, tPA, calcitonin, ANF, EPO and insulin; (n) anti-infective agents such as antifungals, anti-virals, antihelminths, antiseptics and antibiotics; and (m) oxygen, hemoglobin, nitric or sliver oxide.

Non-limiting examples of broad categories of useful pharmaceutical agents include the following therapeutic categories: anabolic agents, anesthetic agents, antacids, anti-asthmatic agents, anticholesterolemic and anti-lipid agents, anticoagulants, anti-convulsants, anti-diarrheals, antiemetics, anti-infective agents, anti-inflammatory agents, anti-manic agents, anti-nauseants, antineoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and prodrugs.

Examples of specific drugs that can be used include: asparaginase, bleomycin, busulfan, capecitabine, carboplatin, carmustine, chlorambucil, cisplatin, cyclophosphamide, cytarabine, dacarbizine, dactinomycin, daunorubicin, dexrazoxane, docetaxel, doxorubicin, etoposide, floxuridine, fludarabine, fluoruracil, gemcitabine, hydroxyurea, idarubicin, ifosfamide, irinotecan, lomustine, mechlorethamine, melphalan, mercaptopurine, methotrexate, mitomycin, mitotane, mitoxantrone, paclitaxel, pentostatin, plicamycin, premextred procarbazine, rituximabe, streptozocin, teniposid, thioguanine, thiotepa, vinplastine, vinchristine, and vinorelbine. In some embodiments, the drugs for lung cancer treatment is paclitaxel, pemetrexed, 10-hydrocamptothecin, irinotecan, erlotinibil/gefetinib or derivates of these molecules.

Examples of anticancer, antineoplastic agents are camptothecins. These drugs are antineoplastic by virtue of their ability to inhibit topoisomerase I. Camptothecin is a plant alkaloid isolated from trees indigenous to China and analogs thereof such as 9-aminocamptothecin, 9-nitrocamptothecin, 10-hydroxycamptothecin, 10,11-methylenedioxycamptothecin, 9-nitro-10,11-methylenehydroxycamptothecin, 9-chloro-10,11-methylenehydroxycamptothecin, 9-amino-10,11-methylenehydroxycamptothecin, 7-ethyl-10-hydroxycamptothecin (SN-38), topotecan, DX-8951, Lurtotecan (G11147221 C), and other analogs (collectively referred to herein as camptothecin drugs) are presently under study worldwide in research laboratories for treatment of colon, breast, and other cancers.

Additionally, the pharmaceutical agent can be a radiosensitizer, such as metoclopramide, sensamide or neusensamide (manufactured by Oxigene); profiromycin (made by Vion); RSR13 (made by Allos); THYMITAQ® (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); L1X (made by Terrapin); agents that minimize hypoxia, and the like.

The agent can be selected from a biologically active substance. The biologically active substance can be selected from the group consisting of peptides, poly-peptides, proteins, amino acids, polysaccharides, growth factors, hormones, anti-angiogenesis factors, interferons or cytokines, elements, and pro-drugs. In useful embodiments, the biologically active substance is a therapeutic drug or pro-drug, in some embodiments, a drug selected from the group consisting of chemotherapeutic agents and other antineoplastics such as paclitaxel, antibiotics, anti-virals, antifungals, anesthetics, antihelminths, anti-inflammatories, and anticoagulants. In certain useful embodiments, the therapeutic drug or pro-drug is selected from the group consisting of chemotherapeutic agents and other antineoplastics such as paclitaxel, carboplatin and cisplatin; nitrosourea alkylating antineoplastic agents, such as carmustine (BCNU); fluorouracil (5-FU) and gemcitabine; hormonal antineoplastics, such as goserelin, leuprolide, and tamoxifen; receptor inhibitors such as erlotinib, gefetinib, sutent or anti-ckit inhibitors, such as GLEEVEC®; natural antineoplastics, such as aldesleukin, interleukin-2, docetaxel, etoposide (VP-16), interferon alpha, paclitaxel, and tretinoin (ATRA).

In another embodiment, the biologically active substance is a nucleic acid sequence. The nucleic acid sequence can be selected from among any DNA or RNA sequence. In certain embodiments, the biologically active substance is a DNA sequence that encodes a genetic marker selected from among luciferase gene, β-galactosidase gene, resistance, neomycin resistance, and chloramphenicol acetyl transferase. In certain embodiments, the biologically active substance is a DNA sequence that encodes a lectin, a mannose receptor, a sialoadhesin, or a retroviral transactivating factor. In certain embodiments, the biologically active substance is a DNA sequence that encodes a RNA selected from the group consisting of a sense RNA; an antisense RNA, siRNA and a ribozyme.

Biologically active agents amenable for use with the new polymers described herein include, without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. Useful active agents amenable for use in the new compositions include growth factors, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are preferred. Members of the TGF supergene family include the beta-transforming growth factors (for example, TGF-b1, TGF-b2, and TGF-b3); bone morphogenetic proteins (for example, BMP-1, BMP-2, BMP-3, BMP-4, BMP-5, BMP-6, BMP-7, BMP-8, and BMP-9); heparin-binding growth factors (for example, fibroblast growth factor (FGF), epidermal growth factor (EGF), platelet-derived growth factor (PDGF), and insulin-like growth factor (IGF)); inhibins (for example, Inhibin A, Inhibin B); growth differentiating factors (for example, GDF-1); and activins (for example, Activin A, Activin B, and Activin AB).

In some embodiments, each of the bioactive agents is independently selected from the group consisting of an antibiotic, an antimitotic, an anti-inflammatory agent, a growth factor, a targeting compound, a cytokine, an immunotoxin, an anti-tumor antibody, an anti-angiogenic agent, an anti-edema agent, a radiosensitizer, and a chemotherapeutic. In some embodiments, at least one of the one or more independently selected bioactive agents is camptothecin. In some embodiments, at least one of the one or more independently selected bioactive agents is 10-hydroxycamptothecin. In some embodiments, at least one of the one or more independently selected bioactive agents is paclitaxel.

In some embodiments, at least one of the one or more independently selected bioactive agents is a platinum containing molecule. In some embodiments, the platinum containing molecule is selected from the group consisting of cisplatin and carboplatinum.

In some embodiments, at least one of the one or more independently selected bioactive agents is a chemotherapeutic agent. In some embodiments, the chemotherapeutic agent is present in at least one polymer coating at a loading of from about one-tenth to about 80 percent by weight. In some embodiments, at least one bioactive agent is present in at least one polymer coating at a loading of from about one-tenth to about 80 percent by weight.

In some embodiments, the chemotherapeutic agent is a drug useful for treating breast, ovarian, or non-small cell lung cancer.

In some embodiments, the chemotherapeutic agent is released from the composite with linear or first order kinetics.

In some embodiments, the chemotherapeutic agent is released from the composite over a time frame effective to inhibit tumor growth or prevent metastasis when the composite is fixated to the tissue surface at the site of disease. In some embodiments, the chemotherapeutic agent is released from the composite over a time frame effective to prevent tumor recurrence when the composite is fixated to tumor resection margins following surgery. In some embodiments, the bioactive agent is paclitaxel.

In some embodiments, at least one of the one or more independently selected bioactive agents is released from the composite over a time frame of at least about 7 days, when fixated to a tissue surface. In some embodiments, the time frame is at least about 30 days. In some embodiments, the time frame is at least about 60 days.

In some embodiments, at least one bioactive agent is present in at least one of the polymer coatings at a loading of from about one-tenth to about 80 percent by weight.

In some embodiments:
the scaffolding material includes one or more materials independently selected from the group consisting of a polyester, a polycarbonate, a polyamide, a polyether, a polyanhydride, a copolymer thereof, collagen, modified collagen, hylauronic acid, and a natural polymer;
each polymer coating includes one or more polymers independently selected from the group consisting of a polyester, a polycarbonate, a polyamide, a polyether, a polyanhydride, and a copolymer thereof;
at least one of the one or more independently selected bioactive agents is a chemotherapeutic agent; and
the chemotherapeutic agent is present in at least one polymer coating at a loading of from about one-tenth to about 80 percent by weight.

In some embodiments, the composite further includes a barrier layer between the scaffolding material and the one or more polymer coatings.

In some embodiments:
the scaffolding material includes collagen;
each polymer coating includes one or more polymers independently selected from the group consisting of poly (caprolactone), poly(lactide-co-glycolide), and poly(g-lycerol monostearate-co-caprolactone);
at least one of the one or more independently selected bioactive agents is selected from the group consisting of camptothecin and paclitaxel; and
at least one of the one or more independently selected bioactive agents is present in at least one polymer coating at a loading of from about one-tenth to about 80 percent by weight.

In some embodiments, the composite further includes a barrier layer between the scaffolding material and the one or more polymer coatings. In some embodiments, the barrier layer comprises poly(lactide-glycolide), poly(trimethylene carbonate), poly(dioxanone), or poly(caprolactone). In some embodiments, the bather layer includes or is made of poly(caprolactone).

Administration to Patients

In some embodiments, the drug-eluting composite will be administered on the surface of cancerous tissue or the site remaining after surgical resection and will release one or more anticancer agents in a gradual and prolonged manner to reduce or kill tumors and/or prevent recurrence or metastasis in tissues including but not limited to lung, colon, ovary, pancreas, mesothelium, connective tissue, stomach, liver, and kidney. In some embodiments, the composite will be administered to the resection margins after local surgery following the removal of a tumor to destroy residual remaining disease and prevent recurrence. The composite can be loaded with one or more prohealing drugs such as anti-inflammatories in addition to anticancer agents to ensure adequate healing of noncancerous tissue. In some embodiments, the composite will be stapled directly over the surface of diseased or treated tissue. The composite implants can also be combined with other therapeutic modalities, including radiotherapy, other chemotherapeutic agents administered systemically or locally, immunotherapy, or radiofrequency ablation. In some embodiments, the composites are administered to the site of disease utilizing methods currently used during standard surgical resection procedures, for example by simultaneously administering the composite using the surgical stapler during the removal of the primary tumor. By the appropriate selection of scaffolding material, therapeutic agent, and drug-eluting material, a compliant composite capable of controlled release of a therapeutic agent to the surface of a tissue can be constructed.

In some embodiments, the present invention provides methods of administering one or more bioactive agent to a patient in need thereof, by implanting the composite in the patient. In some embodiments, the present invention provides methods of administering localized chemotherapeutic treatment to a patient in need thereof, comprising implanting the composite in the patient, wherein at least one of the one or more independently selected bioactive agents is a chemotherapeutic agent. In some embodiments, the localized treatment is at the resection margins to prevent recurrent tumor establishment or metastasis following surgery wherein the systemic administration of chemotherapy, radiation or other traditional treatment methods are ineffective or result in significant morbidity to the patient. In some embodiments, the chemotherapeutic agent is released at the site of disease for at least 7 days.

In some embodiments, the implanting comprises surgically stapling the composite in direct contact with the tissue surface at the site of disease. In some embodiments, the implanting comprises suturing the composite in direct contact with the tissue surface at the site of disease. In some embodiments, the implanting comprises adhering the composite in direct contact with the tissue surface at the site of disease using an adhesive or glue.

In some embodiments, the method further comprises administering radiation.

In some embodiments, the implanting is at the surface of the lung or resection margins at the surface of the lung. In some embodiments, the implanting is at the surface of the lung or resection margins at the surface of the colon. In some embodiments, the implanting is at the surface of the lung or resection margins at the surface of the pancreas. In some embodiments, the implanting is at the surface of the lung or resection margins at the surface of the ovary.

The methods of administration can be used to administer any of the embodiments of the composites described herein, or combination thereof.

This application claims the benefit of priority of U.S. Prov. Appl. Ser. No. 61/052,964, filed May 13, 2008, which is incorporated herein by reference in its entirety.

It is further appreciated that certain features of the invention, which are, for clarity, described in the context of separate embodiments, can also be provided in combination in a single embodiment.

EXAMPLES

The present invention will be further understood by reference to the following non-limiting examples.

Example 1

Formation of Polymer Films on the Surface of Collagen-Based Scaffolding Materials Films were cast from polymer solutions onto collagen-based scaffolds using a microsyringe. First, 10-hydroxy-camptothecin (HCPT) was added to methylene chloride (0.1% w/v) in a glass vial and homogenized for 60 min in a sonication bath to break apart aggregates. Polymer (5% w/v) was then dissolved into the solution by vortexing for 1 min. The solution was slowly added to the scaffold surface and left to evaporate for 24 h, followed by further drying under reduced pressure for another 24 h. Polymer coatings were formed in this manner using poly(lactide-co-glycolide) or poly(caprolactone) or poly(glycerol monostearate-co-caprolactone). For the poly(glycerol monostearate-co-caprolactone) the monomer ratio in the final polymer was about 20:80 and the molecular weight was about 10,000 Da. The molecular weight for the poly(caprolactone) was about 30,000 Da. The poly(lactide-co-glycolide) was from 65,000 to 110,000 Da.

Example 2

Use of a Barrier Film to Promote Adherence of Drug-Eluting Polymer and Scaffolding Material Many scaffolding materials consist of woven fibers or porous material, thus certain polymer solutions permeate quickly through the material instead of forming a distinct polymer coating on top of the scaffold. It was demonstrated that a barrier could first be cast from polymer solutions formulated to be viscous enough to resist penetration into the scaffolding material. The required viscosity is highly dependent on polymer and organic solvent. A barrier layer comprised of poly(caprolactone) was cast from a solution of methylene chloride onto collagen-based scaffolds to form a smooth coating at the surface of the scaffold. One to several polymer coastings were then applied over the poly(caprolactone) layer from solutions of methylene chloride and 10-hydroxycamptothecin or paclitaxel and poly(lactide-co-glycolide), poly(caprolactone), or poly(glycerol monostearate-co-caprolactone) at various polymer concentrations (0.5%-20% w/v). For the poly(glycerol monostearate-co-caprolactone), the monomer ratio in the final polymer was about 20:80 and the molecular weight was about 10,000 Da. The molecular weight for the poly(caprolactone) was about 30,000 Da. The poly(lactide-co-glycolide) was from 65,000 to 110,000 Da.

Example 3

Release of 10-Hydroxycamptothecin from Polymer-Collagen Composites

Using the procedures from Example 2, a composite was constructed from a collagen-based scaffold with a poly(caprolactone) barrier layer and two 10-hydroxycaptothecin-loaded (2% w/w) poly(glycerol monostearate) layers. The composites were submerged in 0.150 mL of PBS at 37° C. At specific time points, an aliquot of release media was removed and the concentration of HCPT was measured by fluorescence spectroscopy ($\lambda_{Ex}$=382 nm and $\lambda_{Em}$=550 nm, Photon Technology International QM-4/2005 spectrofluorimeter). A calibration curve was constructed from nine samples of known HCPT concentrations with linearity observed from 10 nM to 5 µM ($R^2$=0.999) from which the drug concentration of each aliquot was determined. After the completion of release, the HCPT remaining in each film was quantified. Films were dissolved $CH_2Cl_2$ to release encapsulated drug, the solvent evaporated, and PBS (150 mL) was added under rigorous stirring. The fluorescence spectrum was recorded and remaining drug measured.

10-hydroxycamptothecin was released in a prolonged and controlled manner, initially releasing about 10% over the first 24 hours, 2% loading per day for the first two weeks, decreasing to approximately 1% per day for the following three weeks, before diminishing to 0.5% release per day, with continued release detected for at least 6 weeks. The release kinetics of the drug-loaded polymer from collagen-based substrates was similar to films cast on glass supports, suggesting that the scaffolding material does not profoundly affect release kinetics.

Example 4

Prevention of Local Tumor Establishment in a Subcutaneous Lung Cancer Model

Composites described in Example 3 were evaluated in mice to prevent local tumor establishment. C57BL/6 female mice were shaved and cleaned using betadine under Ketamine/Xylazine anesthesia. An incision of 0.8 cm was made between the shoulders on the back of the mice. The connective tissue under the skin was dissected with a pair of sterilized tweezers to make a subcutaneous pocket. Loaded or unloaded UV-sterilized composites (1.0×0.8 cm) were inserted into the subcutaneous pockets and the incision was closed with 5-0 sutures. Two days were allowed for healing of the incision, before 750,000 mouse LLC tumor cells suspended in 0.1 mL of PBS were injected subcutaneously on top of the implanted film via a 27-guage needle. Tumor size was monitored biweekly and animals were euthanized if tumors reached 2 cm in size.

Local tumor growth was defined as the development of subcutaneous tumor nodules within a 0.5 cm radius of the implanted films and did not occur in any of the experimental mice that received the polymer films loaded with HCPT (~0.4 µg/mm$^2$). This is in contrast to the significant tumor growth that occurred directly on top of the unloaded polymer films in nearly 80% of the animals receiving these control films (Figure C9). The local nature of HCPT release is evident in the delayed development of small regional tumors outside the 0.5 cm periphery of the HCPT-loaded polymer films, when tumor cells gained access to distant areas of the subcutaneous pocket as a result of extensive surgical dissection and unintended spreading of the initial injection of malignant cells far away from the film. Notably, in mice treated with unloaded or HCPT-loaded films, the surgical wound healed and significant inflammation was not noted in the chest wall tissues immediately adjacent to either film.

Example 5

Prevention of Tumor Recurrence Using Paclitaxel-Loaded Composites in a Lung Cancer Recurrence Model Female C57BL/6 mice at six to eight weeks of age will be obtained from Jackson Laboratories (Bar Harbor, Me.). A primary tumor was induced by subcutaneous injection of 7.5×10$^5$ Lewis Lung Carcinoma (LLC) cells (in 0.2 mL PBS) on the dorsum of Female C57BL/6 via a 27-gauge needle attached to a 1 mL syringe. This tumor dose effectively results in rapidly progressive tumor within 2 weeks. Tumor volume was estimated by the formula (length×width×height×Pi)/6, and the primary tumor was surgically removed: when the tumor reached 500 mm$^2$. There was no difference in the average tumor, size (588±160 vs 581±96 mm$^3$) between mice that received unloaded films or Pax-films. This size was chosen as the majority of animals will develop locally recurrent tumor despite aggressive surgical resection if no additional therapeutic intervention is performed to prevent recurrent disease. Unloaded or paclitaxel-loaded composites (1.0×0.8 cm; 10% w/w), similar to those described in Example 3, were implanted with the polymer abutting the area of surgical resection. The four corners of the pericardial strip were sutured to the superficial fascia to secure the position of the strip and the skin incision is closed with 5-0 polypropylene sutures. Tumor controls were utilized where no additional therapy was given following surgical resection to establish the incidence of recurrence in these experiments.

All mice treated with unloaded films (n=3) had visible local recurrence at the site of the film at 7.3±1.8 days after resection and required sacrifice secondary to large locally recurrent tumor by 15.6±1.5 days. In contrast, there was no evidence of locally recurrent disease at the site of Pax-films in any of the recipient mice (n=4) at 20 days (p<0.05 vs unloaded films, Fisher Exact Test; Figure). Implantation of Pax-films at the time of surgical resection can prevent local tumor recurrence and prolong survival in a subcutaneous LLC tumor model in mice, without significant impairment in wound healing. These findings suggest that Pax-loaded polymer films incorporated at the surgical margin, can afford enhanced local drug delivery aimed at preventing the growth of occult disease present following parenchyma-sparing surgery, and offer the means to decrease local recurrence rates in patients with stage I lung cancer in the future.

Example 6

Surgical Stapling of a Composite Loaded with 10-Hydroxycamptothecin

A composite described in Example 3 was stapled using a standard thoroscopic surgical stapler and imaged to observe structural features of the stapled films. The SEM micrograph importantly shows that the polymer re-approximates well around the staples and shows no sign of fracturing.

Example 7

Compliance of the Composite

An important property of the composite is its compliance and normalized compliance ratio to tissue. For example after surgical removal of a tumor, the surgical site is repaired and closed with the composite using staples. The composite provides mechanical support to the tissue such that if the tissue is stressed (elongated, compressed) the composite will keep it from re-opening the wound site. Thus the mechanical properties of the composite, composite components, and the tissue are relevant. For example in a lung resection procedure, the margin is repaired using the composite and stapled into place. As the lung tissue expands or stretches, the composite stretches less thus preventing the wound site to re-open. In this example the normalized compliance ratio of tissue to composite would be greater than one.

Example 8

Compliance of the Composite and Comparisons

As described above, an important property of the composite is its compliance and normalized compliance ratio to tissue. The composite provides mechanical support to the tissue such that if the tissue is stressed (elongated, compressed), the composite will keep it from re-opening the wound site. For lung tissue the compressive modulus is about 28 KPa (pig and dog tissue). Certain of the composites described herein have compressive modulus exceeding 1 MPa which contain the scaffolding, barrier/drug eluating layer. As the compliance ratio refers to the ratio of compliance between the tissue and implant, the compliance ratio in this example would be greater than one with the tissue easier to deform than the composite. The larger the compressive modulus the less deformable is the material and, the compressive modulus is greater for the composite than the lung tissue.

Example 9

Rheological Measurements

Samples of tissue or composite were prepared and the mechanical properties of materials were evaluated using an AR1000 rheometer (TA Instruments, New Castle, Del.) A standard 20 mm diameter aluminum parallel plate geometry (TA Instruments, New Castle, Del.) was used to obtain the compressive modulus E, complex shear modulus $|G^*|$, and loss angle $\delta$. The sample was then placed at the center of the temperature controlled bottom platen, and the geometry was lowered to make contact with the hydrogel. A normal force of 0.02 N or greater was applied to the sample to ensure contact through out the testing.

Example 10

Film Thickness on the Scaffolding Material

A barrier layer comprised of poly(caprolactone), poly(lactide-co-glycolide), and poly(glycerol monostearate-co-caprolactone), poly(dioxanone), or poly(trimethylene carbonate) was cast from a solution of methylene chloride onto the collagen-based scaffold to form a smooth coating at the surface of the scaffold. The preferred barrier layer thickness is about 50 microns or greater. This barrier layer enables reproducible and efficient formation of the next polymer layer to be added as well as helps to secure the polymer film to the scaffolding material. Next one to several polymer coasting were applied over the barrier layer from solutions of methylene chloride and 10-hydroxycamptothecin or paclitaxel and poly(lactide-co-glycolide), poly(caprolactone), or poly(glycerol monostearate-co-caprolactone) at various polymer concentrations (0.5%-20% w/v). For the poly(glycerol monostearate-co-caprolactone) the monomer ratio in the final polymer was 20:80 and the molecular weight was about 10,000 Da. The molecular weight for the poly(caprolactone) was about 30,000 Da. The poly(lactide-co-glycolide) was from 65,000 to 110,000 Da.

A number of embodiments of the invention have been described. Nevertheless, it will be understood that various modifications can be made without departing from the spirit and scope of the invention. Accordingly, other embodiments are within the scope of the following claims.

What is claimed is:

1. A compliant composite for delivery of a bioactive agent, comprising a scaffolding material, at least one polymer coating comprising one or more independently selected bioactive agents, and a barrier layer positioned between said scaffolding material and said polymer coating, wherein at least one polymer coating is an oligomer or polymer represented by Formula XXXVIII:

XXXVIII wherein:

each Q' is independently selected from O, S, Se, and NH;

G' is selected from and $R_1$';

$R_1$' is selected from a straight or branched alkyl, cycloalkyl, aryl, olefin, silyl, alkylsilyl, arylsilyl, alkylaryl, arylalkyl, and fluorocarbon chain of 3-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or $R_1$' is selected from poly(ethylene glycol), poly(ethylene oxide), poly(hydroxyacid), a carbohydrate, a protein, a polypeptide, an amino acid, a nucleic acid, a nucleotide, a polynucleotide, any DNA or RNA segment, a lipid, a polysaccharide, an antibody, a pharmaceutical agent, and any epitope for a biological receptor; or $R_1$' is selected from a photocrosslinkable and ionically crosslinkable group; x and y are each independently selected from an integer of 2-750; e is selected from an integer of 1-8; and each polymeric terminal group is selected from hydrogen, amines, thiols, amides, phosphates, sulphates, hydroxides, metals, alkanes, alkenes and alkynes.

2. The composite according to claim 1, wherein G' is $-C(=O)R_1$'; and each Q' is O.

3. The composite according to claim 2, wherein $R_1'$ is selected from a straight or branched alkyl chain of 3-50 carbons.

4. The composite according to claim 1, wherein said scaffolding material comprises one or more materials independently selected from the group consisting of a polyester, a polycarbonate, a polyamide, a polyether, a polyanhydride, a copolymer thereof, collagen, modified collagen, hylauronic acid, and a natural polymer.

5. The composite according to claim 1, wherein said scaffolding material is collagen.

6. The composite according to claim 1, wherein said barrier layer comprises poly(lactide-glycolide), poly(trimethylene carbonate), poly(dioxanone), or poly(caprolactone).

7. The composite according to claim 1, wherein at least one of the one or more independently selected bioactive agents is camptothecin, 10-hydroxycamptothecin, paclitaxel, cisplatin and carboplatinum.

8. The composite according to claim 1, wherein at least one of said one or more independently selected bioactive agents is released from said composite over a time frame of at least about 7 days, when fixated to a tissue surface.

9. The composite according to claim 1, wherein the composite has a normalized compliance ratio of tissue to composite of greater than one.

10. The composite according to claim 1, wherein the composite has a normalized compliance ratio of tissue to composite of from about 0.05 to about 5000.

11. The composite according to claim 8, wherein said time flame is at least about 30 days.

12. The composite according to claim 9, wherein said scaffolding material is a buttressing material.

13. A method of administering one or more bioactive agent to a patient in need thereof, comprising implanting said composite of claim 1 to said patient.

\* \* \* \* \*

UNITED STATES PATENT AND TRADEMARK OFFICE
CERTIFICATE OF CORRECTION

PATENT NO. : 8,795,707 B2  
APPLICATION NO. : 12/991944  
DATED : August 5, 2014  
INVENTOR(S) : Jesse Wolinsky, Mark W. Grinstaff and Yolanda L. Colson Page 1 of 1

It is certified that error appears in the above-identified patent and that said Letters Patent is hereby corrected as shown below:

Title page (Other Publications), delete "Charcterization" and insert -- Characterization --, therefor.

(Other Publications), delete "Photgpatternable" and insert -- Photopatternable --, therefor.

(Other Publications), delete "Photgpatternable" and insert -- Photopatternable --, therefor.

(Other Publications), delete "Dioxacycloheane" and insert -- Dioxacyclohexane --, therefor.

Page 2, col. 1, (Other Publications), delete "Mesomorphouse" and insert -- Mesomorphous --, therefor.

Page 2, col. 2, (Other Publications), delete "nomcl/" and insert -- nomc1/ --, therefor.

Specification

Col. 1, line 8, delete "May 13, 2010," and insert -- May 13, 2008, --, therefor.

Claims

Col. 29, line 8, in Claim 4, delete "hylauronic" and insert -- hyaluronic --, therefor.

Col. 30, line 12, in Claim 11, delete "flame" and insert -- frame --, therefor.

Signed and Sealed this  
Tenth Day of November, 2015

Michelle K. Lee  
*Director of the United States Patent and Trademark Office*